(12) United States Patent
Barry

(10) Patent No.: US 11,932,563 B2
(45) Date of Patent: *Mar. 19, 2024

(54) SYSTEM AND METHOD FOR IMPROVED ANAEROBIC DIGESTION

(71) Applicant: Topstone Ventures, LLC, San Francisco, CA (US)

(72) Inventor: Christopher J. Barry, Ellingham (GB)

(73) Assignee: Topstone Ventures, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/053,298

(22) Filed: Nov. 7, 2022

(65) Prior Publication Data
US 2023/0118918 A1  Apr. 20, 2023

Related U.S. Application Data

(63) Continuation of application No. 17/173,075, filed on Feb. 10, 2021, now Pat. No. 11,492,280, which is a continuation of application No. 16/358,511, filed on Mar. 19, 2019, now Pat. No. 10,947,145, which is a continuation of application No. 15/291,013, filed on Oct. 11, 2016, now Pat. No. 10,233,104, which is a continuation of application No. 14/475,444, filed on Sep. 2, 2014, now Pat. No. 9,481,589.

(60) Provisional application No. 61/872,502, filed on Aug. 30, 2013.

(51) Int. Cl.
*C02F 11/04* (2006.01)
*C02F 3/28* (2023.01)
(Continued)

(52) U.S. Cl.
CPC ............. *C02F 11/04* (2013.01); *C02F 3/28* (2013.01); *C02F 3/2893* (2013.01); *C02F 3/342* (2013.01); *C05F 17/20* (2020.01); *C05F 17/90* (2020.01); *C12P 5/023* (2013.01); *C02F 2303/10* (2013.01); *Y02E 50/30* (2013.01);
(Continued)

(58) Field of Classification Search
CPC .......... C02F 11/04; C02F 3/28; C02F 3/2893; C02F 3/342; C02F 2303/10; C05F 17/20; C05F 17/90; C12P 5/023; Y02E 50/30; Y02P 20/133; Y02P 20/145; Y02W 10/30; Y02W 30/40
USPC ........ 210/603, 606, 611, 252, 259; 435/262, 435/262.5; 71/10
See application file for complete search history.

(56) References Cited

U.S. PATENT DOCUMENTS 5,342,524 A * 8/1994 Gaddy ................. C02F 3/34
                                                                 435/801
6,015,496 A * 1/2000 Khudenko .............. C02F 3/308
                                                                 210/603
(Continued)

FOREIGN PATENT DOCUMENTS

WO    WO 2006/119052 A2 * 11/2006

*Primary Examiner* — Fred Prince
(74) *Attorney, Agent, or Firm* — Kwan & Olynick LLP

(57) ABSTRACT

A method for improved anaerobic digestion is presented. The method includes mixing a volume of waste material with water to form a feedstock mixture. The volume of waste material includes an initial amount of biomass and the feedstock mixture includes methanogenic bacteria either naturally present in the waste material or introduced artificially. The method also includes introducing one or more promoter substances to the feedstock mixture. The one or more promoter substances are capable of modifying the methanogenic bacteria. Modifying includes stimulating novel enzyme production in the methanogenic bacteria.

20 Claims, 5 Drawing Sheets

(51) Int. Cl.
  *C02F 3/34* (2023.01)
  *C05F 17/20* (2020.01)
  *C05F 17/90* (2020.01)
  *C12P 5/02* (2006.01)

(52) U.S. Cl.
  CPC ........... *Y02P 20/133* (2015.11); *Y02P 20/145* (2015.11); *Y02W 10/30* (2015.05); *Y02W 30/40* (2015.05)

(56) References Cited

U.S. PATENT DOCUMENTS

| | | | | |
|---|---|---|---|---|
| 6,254,775 B1* | 7/2001 | McElvaney | ............ | C12M 25/06 210/603 |
| 9,481,589 B2* | 11/2016 | Barry | ...................... | C05F 17/90 |
| 10,233,104 B2* | 3/2019 | Barry | ...................... | C05F 17/20 |
| 2006/0086659 A1* | 4/2006 | Szwajcer Dey | ......... | C02F 3/342 210/603 |
| 2010/0047793 A1* | 2/2010 | Toledo | .................... | C12P 5/023 435/243 |
| 2010/0189706 A1* | 7/2010 | Chang | ...................... | A61P 1/14 435/417 |
| 2010/0252498 A1* | 10/2010 | Ott | ............................ | C02F 9/00 210/205 |
| 2011/0008865 A1* | 1/2011 | Lee | ........................ | C12M 45/04 435/166 |
| 2012/0021477 A1* | 1/2012 | Bernard | ................. | C12M 21/02 435/297.1 |
| 2015/0031913 A1* | 1/2015 | Godlewski | .............. | C07C 51/48 562/599 |
| 2015/0060356 A1* | 3/2015 | Barry | .................... | C02F 3/2893 210/603 |
| 2017/0029310 A1* | 2/2017 | Barry | ...................... | C12P 5/023 |
| 2019/0276344 A1* | 9/2019 | Barry | .................... | C02F 3/2893 |

\* cited by examiner

SYSTEM AND METHOD FOR IMPROVED ANAEROBIC DIGESTION

CROSS-REFERENCE TO RELATED APPLICATIONS

This application is a continuation of U.S. patent application Ser. No. 16/358,511, entitled "SYSTEM AND METHOD FOR IMPROVED ANAEROBIC DIGESTION", filed on Mar. 19, 2019, which is a continuation of U.S. patent application Ser. No. 15/291,013, entitled "SYSTEM AND METHOD FOR IMPROVED ANAEROBIC DIGESTION", filed Oct. 11, 2016, which is a continuation of U.S. patent application Ser. No. 14/475,444, entitled "SYSTEM AND METHOD FOR IMPROVED ANAEROBIC DIGESTION", filed on Sep. 2, 2014, which claims priority to U.S. Provisional Patent Application No. 61/872,502, entitled "SYSTEM AND METHOD FOR IMPROVED ANAEROBIC DIGESTION", filed on Aug. 30, 2013, all of which are incorporated herein by reference for all purposes.

TECHNICAL FIELD

The disclosed embodiments relate generally to anaerobic digestion.

BACKGROUND

Anaerobic digestion is a collection of processes wherein bacteria breakdown organic biomass without the presence of oxygen. Examples of resulting products of anaerobic digestion are methane and carbon dioxide. These biogas products can be used directly for fuel, e.g. in heat and power gas engines, or converted to other forms of renewable energy, e.g. natural gas.

The process of anaerobic digestion typically begins with bacterial hydrolysis of the input materials. Insoluble organic polymers, e.g. carbohydrates, are broken down to soluble derivatives that become available for other bacteria. Acidogenic bacteria then convert the soluble derivatives, e.g. sugars and amino acids, into carbon dioxide, hydrogen, ammonia, and short chain fatty acids (also known as "volatile fatty acids" or VFA). Finally, methanogenic bacteria, or methanogens, convert the VFA to methane and carbon dioxide. In some processes, an intermediate step called acetogenesis occurs where the acidogenic bacteria convert VFAs into acetic acid, which the methanogens utilize in the production of methane and carbon dioxide.

The breakdown of complex polymers during anaerobic digestion is typically slow and inefficient with typical values for the conversion of the volatile solids, which are the main reservoir of these compounds, within the range of 0.1% to 10% of the total amount of available solids. In addition, the ecosystem of the bacterial milieu can be very fragile and sensitive to changes in feedstock and to the surrounding bacterial environment. Thus, there exists a need for improved methods and processes for facilitating anaerobic digestion and increasing the efficiency and resiliency of such processes.

SUMMARY

A method for improved anaerobic digestion is presented. The method includes mixing a volume of waste material with water to form a feedstock mixture. The volume of waste material includes an initial amount of biomass and the feedstock mixture includes methanogenic bacteria either naturally present in the waste material or introduced artificially. The method also includes introducing one or more promoter substances to the feedstock mixture. The one or more promoter substances are capable of modifying the methanogenic bacteria. Modifying includes stimulating novel enzyme production in the methanogenic bacteria.

In some embodiments, the method includes removing large solids from the feedstock mixture. In some embodiments, the method includes collecting renewable energy or biochemical co-products generated from digestion of the waste material in the feedstock mixture. In some embodiments, the biochemical co-products include fertilizer, vitamins, or proteins. In some embodiments, the methanogenic bacteria or the waste stream, or both, are pre-treated with a solution of enzymes before any anaerobic digestion processes occur. In some embodiments, stimulating novel enzyme production includes increasing the expression rate of already expressed genes to a level statistically significantly higher than that of methanogenic bacteria not exposed to the promoter substances or stimulating the expression of genes useful for anaerobic digestion that are usually unexpressed in methanogenic bacteria not exposed to the promoter substances. In some embodiments, the methanogenic bacteria are cultured from resident populations in the volume of waste material so as to reduce barriers to bacterial adaptation to the feedstock mixture. In some embodiments, the method includes introducing additional methanogenic bacteria into the feedstock mixture to speed up anaerobic digestion. In some embodiments, modifying the methanogenic bacteria includes modifying the bacteria in a way as to eliminate the need for acidogenesis to occur more than once or the need to even occur at all during the process of methanogenesis.

In some embodiments, the one or more promoter substances includes an enzyme that converts a portion of the biomass into promoter molecules such as cellobiose, glucose, xylose, mannose, or maltose or wherein the one or more promoter substances includes promoter molecules themselves. In some embodiments, anaerobic digestion occurs in the presence of VFA levels above the maximum VFA level at which acidogenic bacteria can survive. In some embodiments, collecting renewable energy includes monitoring and sequestering methane and carbon dioxide generated from the blend, as well as returning the sequestered carbon dioxide back into a digester as substrate for further methane production. In some embodiments, collecting renewable energy includes subjecting gas generated to a scrubber system and storing scrubbed gas in a fuel storage tank or converting the scrubbed gas into other forms of renewable energy. In some embodiments, collecting renewable energy comprises recovering liquefied biomass residues and residual solids for further processing into other forms of fuel or other materials for usage.

In some embodiments, the methanogenic bacteria attain species dominance over competing non-methanogenic bacteria in a digester. In some embodiments, the one or more promoter substances leads to fatty acid production in concentration levels above the maximum levels that are tolerable for acidogenic bacteria. In some embodiments, the method is performed without a pasteurization step. In some embodiments, at least some of the modified methanogenic bacteria are adapted to utilize directly as a food source a wide range of substrate forms and feedstock streams, including oligosaccharides, polysaccharides (cellulose and starch), monosaccharides, other sugars, amino acids, short chain alcohols, and volatile fatty acids. In some embodiments, the volume of waste material includes a mixed waste stream containing both bio-organic and non-bio-organic material, such as plastic or metal materials, wherein the non-bio-organic material is separated from the mixed waste stream and processed into forms suitable for reuse.

In some implementations of the present disclosure, a system for improved anaerobic digestion is provided. The method includes machinery configured to carry out the methods presented in the present disclosure.

BRIEF DESCRIPTION OF THE DRAWINGS

Like reference numerals refer to corresponding parts throughout the drawings.

DESCRIPTION OF EMBODIMENTS

Figure 1:
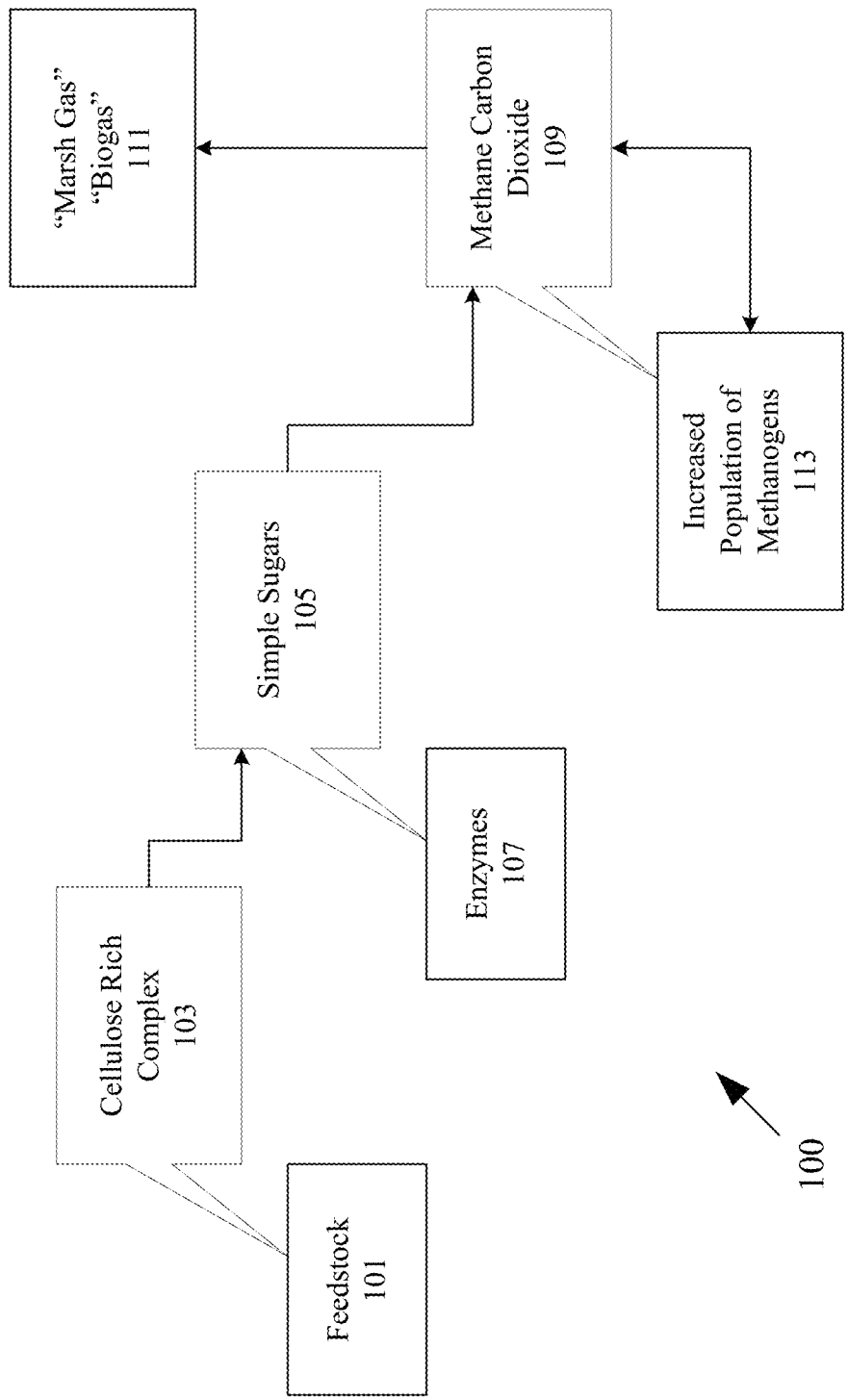
FIG. 1 is a flow diagram illustrating the general concept of anaerobic digestion, in accordance with the present disclosure.

It will be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

As used herein, "organic" refers to any substance based on the concatenation of carbon atoms. Such substances include, but are not limited to: plastics, rubber and rubber analogues, carbohydrates, polymeric, oligomeric and single structures found repeating in the fore mentioned higher order moieties. Such substances also include: proteins, amino acids, fats, fatty acids and their esters.

As used herein, "bio organic" refers to organic substances that are directly associated with living organisms and derived therefrom.

As used herein, "plastic" refers to any organic substance comprised of long chains of carbon atoms or carbon based subunits referred to as plastics in normal usage. This will include, but is not limited to: PET, HDPE, LDPE, PVC, and PPE.

As used herein, "anaerobic digestion" and "fermentation" both refer to the extraction of energy from carbon compounds as a function of the catabolic metabolism of specific microorganisms and leading to the generation of compounds which are combustible and usable in systems designed to convert chemical energy held in the chemical bonds of the compound into motion, heat or light through the oxidative splitting of those bonds.

As used herein, the terms "methanogenic archaea," "methanogenic bacteria," and "methanogens" are used interchangeably.

As used herein, the terms "competing organisms" and "acidogenic bacteria" refer to non-methane producing bacteria.

As used herein, the terms "mg per liter" (or "mg/L") and "parts per million" (or "ppm") are used interchangeably.

As used herein, the term "modify" with regards to bacteria refers to inducing the bacteria to either produce more enzymes than normal and/or new enzymes or reduce the production of some enzymes thus allowing noticeably more efficient anaerobic digestive processes.

As used herein, the term "noticeably" refers to either a statistically significant change or an observable difference by one of ordinary skill in the art.

Reference will now be made in detail to various embodiments, examples of which are illustrated in the accompanying drawings. In the following detailed description, numerous specific details are set forth in order to provide a thorough understanding of the present disclosure and the described embodiments. However, the present disclosure may be practiced without these specific details. In other instances, well-known methods, procedures, components, and circuits have not been described in detail so as not to unnecessarily obscure aspects of the embodiments.

Overview

Some embodiments of the present disclosure provide a means to reduce the manpower employed in sorting waste for recycling and utilizes biochemical and chemical means to convert the organic fraction of waste (normally approximately 70%) in municipal waste into useful products of value equal to or exceeding that associated with the previous properties of the materials.

Some embodiments of the present disclosure apply the use of enzymes to clean organic materials and inorganic materials, e.g. plastics, metals, rubber, and carbon based and silicon based fibers and matrices, and enhance their value in general recycling by removing bioorganic contaminants from them.

In some embodiments, the methods and systems provided help to reduce the overall volume of waste. Some embodiments of the present disclosure further utilize the bioorganic residues removed from plastics and other materials by enzyme digestion as a feedstock for advanced anaerobic digestion, along with the digestates of the bulk of the bioorganic residues present in the waste. Some embodiments of the present disclosure return mixed plastics to chemically consistent separate compounds of similar or identical properties to their native form. In addition, in some embodiments, organic substances are removed or cleaned from the surfaces of metals, restoring them to their native state and native reactivity.

Some embodiments of the present disclosure relate to a series of processes which when conjoined in a specific sequence enables bioorganic materials present in waste, which include but are not limited to municipal solid waste, manures or sewage, garden clippings, and agricultural crops, to be efficiently utilized by microorganisms in the generation of organic products suitable for use as fuel or solvents. Some embodiments further relate to the enhancement of value plastics and other non-organic materials for recycling and further processing. In such embodiments, this is accomplished through the digestion of contaminating bioorganic substances as a consequence of passing through pretreatment and/or fermentation mixtures established to yield the fuel and solvent benefits described above.

Some embodiments of the present disclosure further relate to the separation of distinct plastics with coherent physical and chemical properties from an admixture. In such embodiments, this is accomplished through the use of organic solvents and the varying solubilities of the plastics in the mixture, as described using Hildebrand and Hansen parameters. Such plastics, having previously passed through the pretreatment and/or fermentation steps, lead to the digestion of contaminating bio organic residues adhering to or being a part of them. In various embodiments, the separation of plastics techniques are applied to other non-organic materials, such as metals.

In various embodiments, the methods and steps described herein below are directed toward the generation of fuels or organic solvents and of plastics, with physical and chemical properties close to the native forms, from mixed waste streams containing both bio-organic and organic/plastic materials of a variety of forms.

Waste Material Processing
Primary Mixing and Separation

In some embodiments, exemplary processes are chemical and biological, relying on reactivity of the substances in the waste stream under different agencies. In some embodiments, it is desirable to maximize the surface area for interaction between the chemical and biological agents and the waste materials, to ensure maximum area of contact between the reactants. In such embodiments, waste material is thus shredded to maximize surface area. However, in some embodiments, when particles are above a certain particle size, the rate of reaction is slowed down due to the increased viscosity when the material takes up water in the enzyme/separating bath. In such embodiments, this is addressed by steadily adding the material to the mixing bath, ensuring a mixture having no less than 50% water, measured by monitoring the viscosity of the mix in the tank. In some embodiments, the percentage of water is less than 50%. In some implementations, the optimum size for shredding has been found to be between ½" and 1" square particles. However, in other embodiments, particle sizes may vary depending on machinery.

In various embodiments, the shredded material is continuously fed into a continuous stir vessel containing water until a ratio of 1:1 by volume of water to the waste is achieved. In some embodiments, the ratio may vary. In some embodiments, this vessel contains cellulase of not less than 40,000 units per litre and rich in beta glucosidase, as well as other enzymes, including amylase, lipase and protease. In some embodiments, the concentration of cellulase can be less than 40,000 units. In various embodiments, the mixture of enzymes includes different combinations and concentrations of enzymes. For example, some embodiments have only cellulase while other embodiments have cellulase plus other enzymes. In some embodiments, as the sugars are released, they are also being accessed by competing organisms aerobically, and therefore wasted in terms of anaerobic digestion (since the carbon products produced from aerobic digestion by competing organisms will be lost in the form of gas, e.g. $CO_2$, as opposed to the carbon products produced from anaerobic digestion by the same competing organisms, which is retained in the form of usable soluble substrates such as fatty acids). Therefore, in such embodiments a balance between time to generate sugars and their loss by aerobic digestion prior to the anaerobic digestion process needs to be maintained. In some embodiments, the mean time of mixing for any given quantity of waste introduced should exceed 3 hours but not exceed 8 hours. In other embodiments, the timeframe can vary, as long as enough time has passed such that a sufficient amount of sugars is released, yet not too much time has passed such that a significant portion of the sugars is consumed and lost in the process. In some embodiments, the mixing should be vigorous, giving rise to a vortex in the vessel. In some embodiments, the liquid surface in the vessel is skimmed to remove floating materials two hours after the introduction of the last loading of the day. In some embodiments, the floating residues are passed off to plastics processing. The liquid fraction, containing sugars and other fermentable materials in solution, released by enzyme action or naturally present in the liquid fraction, are passed to a fermenter already inoculated with pre-prepared methanogenic microorganisms. In some embodiments, "pre-prepared" includes being pre-treated with a solution of enzymes or promoter molecules. In some embodiments, the high density fraction is collected and the water is removed and passed for further processing.

Removal of Solids

In some embodiments, low density material is skimmed off the surface of the enzyme mixing tank and passed to other avenues for plastic processing. In some embodiments, high density material will remain in the tank and removed periodically and passed for further processing, e.g. plastics processing or metals processing.

Plastics Processing a. Theory

In some embodiments, different plastics have different structures and functional groups within a given polymer, therefore the solubility of any given plastic in any given organic solvent will differ. In some embodiments, a good estimate of the actual solubility of any given plastic in any given solvent or mix of solvents can be reliably achieved using the Hildebrand Algorithm. Actual solubility coefficients for a wide range of plastics in a wide range of solvents have been calculated and tabulated in standard tables of "Hildebrand Parameters." In some embodiments, this theory is applied to enable the separation of PET from other plastics by direct solubility and then, by reducing the solvent by evaporation, to precipitate further dissolved plastics in a progression. In some embodiments, the solvents used include but are not exclusive to Dichloromethane, Hexane, Propanol, and Butanol.

b. Plastic Precipitation

In various embodiments, after plastics have been separated and removed using the processes described above, the plastics are further processed using a variety of processes. One exemplary process is discriminatory precipitation of plastics. In some embodiments, the solvent containing dissolved plastics is subjected to gentle heat, causing evaporation of the solvent, which is captured in a condensing apparatus for recycling. As the solvent evaporates, individual plastics come out of solution and form a film on the surface of the solvent, which can be removed. In some embodiments, each plastic precipitated is collected and flaked or held in a sheet and 'dried' for sale. In various embodiments, a benefit of the processes is the procurement of plastics with similar or identical polymer structures and physical characteristics from a mixed variety of input and the subsequent return of the procured plastics to new product use.

Metals Processing

In various embodiments, metals are separated using chemical, electrolytic, and biological sequestration processes. For example, the separation of copper, after being removed from the tank, is achieved by first dissolving the copper in an acidic solution, thus forming an ionic solution. Then, an electric current is passed through the ionic solution resulting in electrolytic deposition of the pure metal. As a further example, plants or bacteria capable of sequestering metals within their cell walls or elsewhere will be used to concentrate the metals. The plants or bacteria will then be harvested and the metals removed by acid treatment to the plants and bacteria, thereby lysing the cell walls and liberating the metals in ionic form, and enabling the subsequent concentration of the harvested metal ions by electrolysis, as described above.

The various processes described above are examples of processing non-organic materials found in the residual solids in the waste. In various embodiments, other methods can be applied to recover the value of remaining non-organic solids. For example, other methods of recovery include conversion into building materials, recovery of salts by dissolution, and microbial sequestration of silicon.

Advanced Anaerobic Digestion

In various embodiments, waste material, with large solids removed, is passed to an anaerobic fermentation chamber, size range from 1 to 1,000,000 gallons. In some embodiments, in the fermentation chamber, or digester, the waste is mixed continuously, normally by an impeller system. To this mixture may be added a culture of methanogenic organisms which have been exposed to the enzyme generated breakdown products from the waste and shown to be adapted as described, generating their own enzymes to deal with the materials. In some embodiments, the chamber is designed to create overlapping turbulent flow regions to ensure continuous mixing, but minimize cavitation. In some embodiments, the turbulent flow regions increase the exposure of the methanogens to available promoter substances and feedstock. In some embodiments, the methanogens will be cultured from the resident population in the waste, to reduce any barriers to adaptation associated with the general composition of the waste. Alternatively, in some embodiments where the population of methanogens is sufficient, the transition will be engendered in situ, in the main digester and no additional introduction made.

In various embodiments, anaerobic digestion of biomass to generate methane relies on a cascade of conversions of the biomass into different molecular forms of the carbon skeletons present, ultimately presenting methane generating archaea and bacteria with short chain carboxylic (fatty) acids of carbon chain lengths between 1 carbon and 5 carbons.

In some embodiments, shorter chain sugars are able to interact with the microbial cells in two ways: First, the sugars and other short chain molecules can be metabolized anaerobically by some bacteria (notably of the genus clostridia or group referred to as bacilli) with the result that these organisms generate Short Chain Fatty Acids (Volatile Fatty Acids, or VFA). These VFA's are readily acceptable as food for conversion to methane and carbon dioxide by methanogenic microbes of the methanogenic archaea, such as *Methanosarcina* Spp. and Methanogenic bacilli, such as *Methanobacillus* Spp., which is one type of prokaryotic microorganism. Second, the smaller sugar molecules are able to interact with the methanogenic cells directly, for example to promote the generation of additional enzymes by the cells which enable them to access both the shorter chain sugars and polymers of sugars in addition to the VFAs.

In some embodiments, the methanogenic archaea and bacteria convert these to methane and carbon dioxide in approximately equimolar quantities. In other embodiments, either methane or carbon dioxide is produced in greater quantities. In some embodiments, the transformation of the biomass to the short chain carboxylic acid moieties is accomplished by the fermentation of the sugars by other bacteria present in the milieu, e.g. acidogenic bacteria such as Clostridia and Bacilli. In some embodiments, fermentation can also be accomplished through other means, such as yeast fermentation. In some embodiments, there is substantial loss of energy from the final food available to the methanogenic archaea and bacteria, since the bacteria carrying out the conversion utilize energy and resources in their own life processes.

In various embodiments, methanogenic archaea and bacteria are capable of utilizing carbohydrate polymers and simple sugars and carbon dioxide as well as other molecules to generate methane and sustain their own life processes. However, in such embodiments, it is necessary to stimulate the generation of necessary enzymes in the methanogenic archaea and bacteria in order to exploit this capability, because normal unstimulated methanogens do not produce as much enzyme activity as the stimulated versions. In some embodiments, this stimulation is referred to as "promoter modification," or simply "modification," of the methanogenic bacteria. In some methanogenic archaea and in other bacterial systems, genes coding for the enzymes to carry out specific catabolisms are stimulated by pre-exposing the methanogenic bacteria to promoter substances. In such systems, the pre-exposure, or pre-treatment, causes the generation of specific enzyme groups within the methanogenic bacteria, in order to commence transcription and translation activities in the presence of the molecules with which they will need to break down in order to generate methane, or smaller products of these molecules, where the molecules concerned are polymers of very high molecular weight. More specifically, some methanogenic bacteria are modified by the presence of sugars, in particular cellobiose, which stimulate generation of new enzymes. The enzymes cause the breakdown of the very large polymers of glucose—cellulose and hemicellulose—into smaller units. These smaller units can penetrate the cell membrane of the methanogenic bacteria and interact with the genome causing the bacteria to generate multiple copies of genes, coding for necessary enzymes, in the form of RNA, which is the messenger substance that is then decoded in the cell, and translated into sequences of amino acids, or proteins. The particular proteins are the enzymes for which the genome and the RNA copies are coding. Thus, the smaller molecules stimulate the "switching on" of genes coding for the enzymes desired. In some embodiments, cellobiose is the smallest fragment of cellulose released (two glucose molecules bound together) and acts as a promoter molecule.

In some embodiments, the specific enzyme groups promoted include a wide variety of different enzyme groups. In some embodiments, promoter substances are enzymes that break down waste material or feedstock into promoter molecules, e.g. cellobiose, glucose, xylose, mannose, or maltose, which in turn cause the methanogenic bacteria to produce the aforementioned specific enzyme groups. In other embodiments, promoter substances are just the promoter molecules themselves. For example, a batch of methanogenic bacteria alongside waste materials are pre-treated with a promoter substance, e.g. cellulase or cellobiose, such that the batch of methanogenic bacteria uptake the promoter substance within the methanogenic bacterial cells thereby promoting generation of novel enzyme groups, e.g. cellulase, amylase, or lipases, within the methanogenic bacteria which normally would not be produced via gene expression in any significant concentrations within unmodified methanogenic bacteria. In yet other embodiments, the promoter substances are a mix of enzymes and the promoter molecules themselves.

In various embodiments, the organisms normally involved in the cascade leading to the generation of the short chain carboxylic acids in the conventional anaerobic digestion process, referred to above as "acidogenic bacteria," are disabled or killed at high concentrations of the carboxylic acids (aka volatile fatty acids or VFAs) they produce, e.g. above 5000 mg per liter (or ppm) because such concentrations are toxic to the very organisms that generate them. In some embodiments, as a consequence of the disablement of the carboxylic acid generating bacteria by high concentrations of their products (the VFAs), the concentration of the VFAs are kept below 5000 mg per liter in order to preserve the role of acidogenic bacteria in anaerobic digestion. In other embodiments of the present disclosure, the concentrations of the VFAs are allowed to reach well over 5000 mg per liter, due to the advantages of utilizing sugars directly, thereby obviating the role of acidogenic bacteria in anaerobic respiration, as a result of promoter modification of the methanogenic bacteria. In such embodiments, the flood of sugars and similar substances generated by the pre-treatment of purified enzymes causes an upsurge in metabolism in the VFA producing organisms and consequent rapid increase in the VFA concentration. This in turn causes an increase in methanogenic activity and a converse reduction in the VFA (acidogenic) producing activity and the death or disablement of the acidogenic organisms, reducing and then abolishing their competitive advantage over the methanogenic organisms. This then allows the methanogenic organisms to achieve much higher populations and even species dominance in the digester, with consequent increase in the rate of production and volume of methane.

In various embodiments, in each cycle of anaerobic digestion, a pasteurization step is introduced into the anaerobic respiration process in order to reduce the levels of competing organisms, e.g. acidogenic bacteria, after adequate amounts of VFAs have been produced. In such embodiments, pasteurization allows for improved subsequent methanogenic output. In some embodiments, another strategy for reducing the levels of competing organisms is to raise the temperature of the digester contents in order to operate at Thermophilic temperatures, e.g. above 50 degrees Celsius. However, both of these strategies have a high energy demand and also kill methanogenic bacteria, thereby reducing the methanogenic population, as well as the range of methanogenic bacteria types. In such embodiments, the small population of methanogens and the reduced range of different methanogen types render the methanogenic microbial community very volatile and at risk to sudden change, for example in feedstock composition or environmental changes, e.g. temperature or pH level. Thus, in some embodiments of the present disclosure, a pasteurization step is rendered unnecessary by the elevation of the VFA concentrations above the level of tolerance of the competing organisms.

In various embodiments of the present disclosure, cellulase, lipase and protease enzymes are used to stimulate the release of soluble sugars and other carbon compounds from the insoluble volatile solids or polymers. These stimulate the rapid production of short chain carboxylic acids by the acid producing bacteria. The carboxylic acids provide an accessible food source for the methanogenic archaea and bacteria. In some embodiments, enzymes are repeatedly introduced with the objective of generating consistent levels of usable sugars from the waste or feedstock. In other embodiments, enzymes are only introduced once, for example, in an enzyme activity stage, to both break down the feedstock into usable sugars and to stimulate the production of novel enzymes in the methanogenic bacteria. Thus, in some embodiments, the smaller chain sugars and or other molecular entities released in the enzyme activity stage promote, through promoter modification, the release of a wider range of catabolic enzymes in the methanogenic bacteria giving them greater access to a wide variety of carbon sources (food) available.

In various embodiments, the use of purified enzymes replaces the activities of microbes in the community present in the initial breakdown of large polymers of sugars, proteins and fats, reducing them to their basic subunits or shorter combinations thereof. In such embodiments, cellulose and starch are reduced to glucose, cellobiose (cellulose product) or maltose (starch product) or longer chains of glucose molecules. This renders the sugars more amenable to further, energy releasing, breakdown by microbes present in the NEXT stage, without loss of energy through the consumption of the material by the microbes. The consumption of large molecules by microbes uses energy, energy that would otherwise be used to convert smaller molecules into useful anaerobic digestion products. Thus, because the enzymes are molecules and, although derived from animate organisms, are themselves inanimate and simply catalyze the change without consuming the substrate (nor are they consumed themselves during the reactions they catalyze), there is less energy being wasted.

Post-Anaerobic Digestion Processes

In various embodiments, the generation of methane and carbon dioxide is monitored and carbon dioxide is sequestered and returned to the digester as a substrate, thus enhancing further the generation of methane, as carbon dioxide will itself be reduced to methane. In some embodiments, any contaminating hydrogen sulfide will be removed by conventional scrubber systems (examples of such systems include microbial sulfide oxidation or iron oxide reduction, but are not exclusive of other scrubber systems). In some embodiments, all gas generated will be passed through this process.

In some embodiments, the scrubbed methane will be passed either to storage and then on to pipeline use for direct domestic and industrial consumption. In some embodiments, the newly scrubbed or stored methane will be passed to a compressor to produce Compressed Natural Gas (CNG) for vehicles and other fuel applications, or to a transducer such as a gas generator of sparking cylinder design or a gas turbine, for combustion with the energy yielded, possibly applied to the generation of electricity.

In some embodiments, liquefied biomass residues and residual solids for the process will be recovered and subjected to further processing to generate high value fertilizer and other high value biochemical products.

Pre-Treatment Detail

In various embodiments, the addition of certain enzymes helps facilitate the breakdown of bio-organics into useful substances to be incorporated in methanogenic metabolism. One example pre-treatment process is described in detail below. In some embodiments, waste material is fed into an aerobic, continuous mixing vessel containing water. In some embodiments, the waste material loaded into the vessel should be about 10-50% mass of waste to volume of water. Next, enzyme mixes, especially those containing cellulases, beta-glucosidases, amylases, lipases, xylanases, and proteases, are added to the vessel. In some embodiments, the mixture is primarily composed of cellulase enzymes because some waste feedstock streams comprise mostly of cellulose.

In some embodiments, the amount of enzyme added is based on constraints in agitation and viscosity, with the enzyme addition ranging from 40,000 to 200,000 units per liter of waste mixture. In some embodiments, the cellulase based enzyme mix is typically added to form concentrations of 115,000 units per liter of waste mixture. In some embodiments, the vessel containing the waste and enzyme mixture is then incubated at 37 degrees Celsius and agitated for 3 to 12 hours, or enough time to break down materials, but not for too prolonged of periods, which allow non-target microorganisms to significantly reproduce and consume the material. In some embodiments, at the end of the enzyme pre-treatment, the waste mixture is then ready to enter into an anaerobic vessel to undergo anaerobic digestion.

In various embodiments, the range of enzyme mixes will be approximately: 115,000 units of cellulase, 44,000 units of beta-glucanase, 3,500 units of xylanase, and 2,500 units of beta-glucosidase. In some embodiments, processing the waste material with this enzyme mix is an important step in the pre-treatment process for anaerobic digestion. The cellulase, beta-glucanase, xylanase, and beta-glucosidase help release the fermentable sugars bound in lignocellulosic material. In some embodiments, pre-treatment of waste material with enzymes alters the physical structure, size of particles, and chemical composition of the waste material. In some embodiments, hydrolysis, the process in which sugar polymers are converted into smaller or single sugar monomers (these small carbohydrate polymers or monomers are fermentable sugars), should be achieved effectively because the fermentable sugars is a useful product for microbial metabolism.

In various embodiments, the waste feedstock is generally rich in lignocellulosic material, which comprises of mostly cellulose by weight, and smaller proportions of hemicellulose and lignin (cellulose is the most abundant organic polymer on Earth). Cellulose is a polysaccharide that consists of a linear chain of several hundred to over ten thousand beta linked D-glucose units, and the cellulase enzymes cleave the cellulose bonds into smaller polymers. Beta-glucanases cleaves large polymers, and xylanases and beta-glucosidases continue the breakdown of long chain polymers into smaller polymers.

In some embodiments, the waste is not sterile and native communities of microorganisms, fungi, and other organisms exist in the feedstock. In such embodiments, these organisms can utilize smaller carbohydrate polymer chains but cannot efficiently or effectively break down large chain polymers. Therefore, in such embodiments, the enzyme pre-treatment mix is inundated with cellulase and beta-glucanase enzymes to speed up the initial break down of cellulose and large chain carbohydrate polymers so that the smaller chain carbohydrates are accessible to microorganisms and fungi.

In some embodiments, the methanogens will be promoted by carbohydrate polymers to excrete enzymes that can break the carbohydrate polymers into fermentable sugars, including but not limited to monosaccharides, disaccharides, and small polysaccharides. In other embodiments, the fermentable sugars will be consumed by microorganisms that will convert the fermentable sugars into volatile fatty acids and then to acetic acid, which methanogens can also utilize as metabolic substrate.

Although the enzyme pretreatment process in various embodiments is predominantly aimed to hydrolyze celluloses, which then allow the native microorganism population to be able to break down the long chained polymers, enzymes that also have the capabilities of breaking down the long chain polymers into smaller chain polymers can also be used. One reason for this is because some enzyme mixes do not need to be a pure enzyme mixes, and purifying the enzyme mixes is a costly process. In some embodiments, waste feedstock streams do not require such levels of enzyme purity.

DETAILED DESCRIPTION OF THE FIGURES

Description of FIG. 1

FIG. 1 is a flow diagram illustrating the general concept of anaerobic digestion, in accordance with the present disclosure. This figure describes an example process 100 whereby a cellulose-rich complex 103 in feedstock 101 is reduced by enzymes 107 to simple sugars 105. In some embodiments, the enzyme activity may be enhanced by the addition of 2% v/v of ethanol which has been shown to accelerate the enzyme activity. In some embodiments, the proportion of the cellulase types can be altered such that the level of activity of betaglucosidase is enhanced above that of endogluconase and exogluconase, thus leading to an increase in the level of glucose by comparison to cellobiose and oligomers thereof. In some embodiments, oligosaccharides and disaccharides are also released in addition to the simple sugar monosaccharides. Through anaerobic digestion by populations of methanogenic bacteria or archaea, the simple sugars are converted first to a range of carboxylic acids utilizing several step metabolic pathways catalyzed by enzyme activity and co-enzyme complexes to ultimately yield methane and carbon dioxide gasses via a terminal acetoclastic step 109. In some embodiments, the uptake of the released glucose and carboxylic acids by the methanogens dictate the rate of enzyme activity since both cellobiose and glucose are end product inhibitors of the cellulase complex. The enhancement of the methanogenic activity therefore or the rapid removal from the cellulase-rich mixture of glucose and cellobiose is critical to the rate of further release of glucose. In some embodiments, the enhancement of the methane generation capability from a range of substrates is an important feature of the anaerobic digestion process. In some embodiments, methane is commonly known as "marsh gas" in a wetland habitat or "biogas" 111 when it is deliberately generated in an anaerobic digester. In some embodiments, acidogenic bacteria (e.g. clostridia, bacilli), or acidogens, convert sugars to volatile fatty acids. The fatty acids are themselves toxic to the acidogens. In some embodiments, the absence of competing bacteria due to the acidifying effect from the released sugars being converted by acidogens results in a relative increase in the population of methanogens 113.

Figure 2:
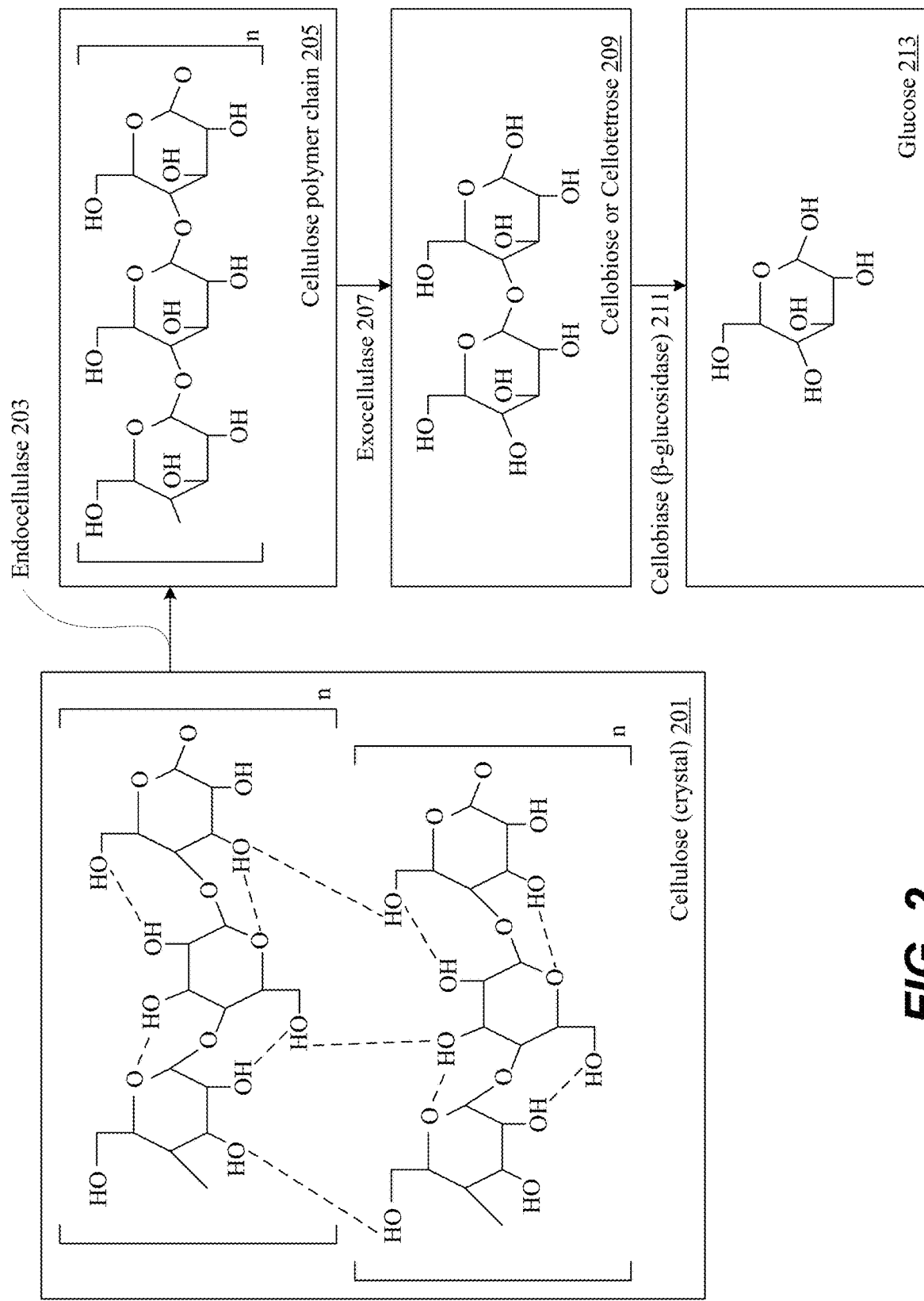
FIG. 2 is a block diagram illustrating example structures of sugars, in accordance with the present disclosure.

Description of FIG. 2

FIG. 2 is a block diagram illustrating example structures of sugars, in accordance with the present disclosure. FIG. 2 depicts an example structure of cellulose crystal 201 that is brought into contact with endocellulase 203. Glucose molecules 213 are released from the cellulose polymer chains 205. Simultaneously, contact between cellulose polymer chains 205 with exocelullase 207 results in the fragmenting of the polymer chains and additional oligosaccharides into two or four glucose units 209, also known as cellobiose or cellotetrose 209. Subsequently, cellobiose 209 is broken into two separate glucose units 213 through the action of beta-glucosidase 211.

Figure 3:
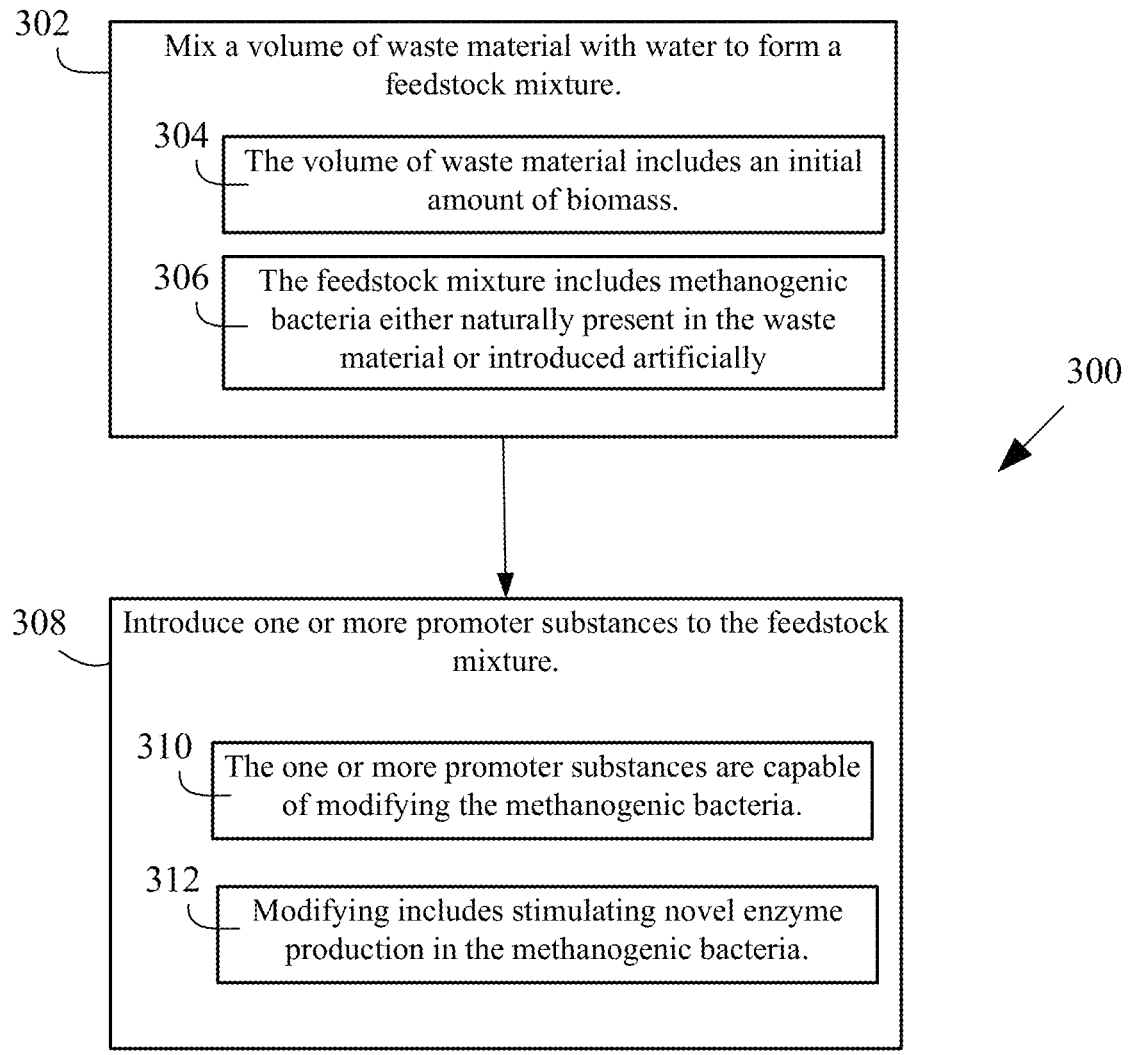
FIG. 3 is a flow diagram of a process for improved anaerobic digestion, in accordance with the present disclosure.

Description of FIG. 3

FIG. 3 is a flow diagram of a process 300 for improved anaerobic digestion, in accordance with the present disclosure. At 302, a volume of waste material is mixed with water to form a feedstock mixture. The amount of water used may vary. In some embodiments, a ratio of 50:50 waste to water volume is used. In some embodiments, the mixing occurs in a digester. In some embodiments, the mixing occurs for a fixed period of time at a speed such that cavitation is minimized. In some embodiments, the volume of waste material includes (304) an initial amount of biomass. In some embodiments, the feedstock mixture includes (306) methanogenic bacteria either naturally present in the waste material or introduced artificially. In some embodiments, the methanogenic bacteria are cultured from resident populations in the volume of waste material so as to reduce barriers to bacterial adaptation to the feedstock mixture. In other embodiments, methanogenic bacteria are cultured elsewhere and then subsequently introduced to the feedstock mixture. In some embodiments, the volume of waste material includes a mixed waste stream containing both bio-organic and non-bio-organic material, such as plastic or metal materials, wherein the non-bio-organic material is separated from the mixed waste stream and processed into forms suitable for reuse. In some embodiments, the methanogenic bacteria or the waste stream, or both, are pre-treated with a solution of enzymes before any anaerobic digestion processes occur. In such embodiments, the pre-treatment is added to speed up the anaerobic digestion processes. An example of a pre-treatment solution is described above in earlier sections of the application.

At 308, one or more promoter substances are introduced to the feedstock mixture. In some embodiments, the one or more substances are capable (310) of modifying the methanogenic bacteria. In some embodiments, the one or more promoter substances are the same as the enzymes used in the pre-treatment solution described above. In other embodiments, the promoter substances are different than the pre-treatment solution enzymes. In some embodiments, modifying includes (312) stimulating novel enzyme production in the methanogenic bacteria. In some embodiments, stimulating novel enzyme production includes increasing the expression rate of already expressed genes to a level statistically significantly higher than that of methanogenic bacteria not exposed to the promoter substances. In some embodiments, stimulating novel enzyme production includes stimulating the expression of genes useful for anaerobic digestion that are usually unexpressed in methanogenic bacteria not exposed to the promoter substances. Thus, in such embodiments, some bacteria are modified such that they produce more enzymes than they normally produce when unmodified by the promoter substances, and some bacteria are modified to produce enzymes from genes that are normally not expressed in unmodified bacteria. In some embodiments, modifying the methanogenic bacteria includes modifying the bacteria in a way as to eliminate the need for acidogenesis to occur more than once. In other embodiments, modifying the methanogenic bacteria includes modifying the bacteria in a way as to eliminate the need for acidogenesis to occur at all during the process of methanogenesis. In some embodiments, at least some of the modified methanogenic bacteria are adapted to utilize directly as a food source a wide range of substrate forms and feedstock streams, including oligosaccharides, polysaccharides (cellulose and starch), monosaccharides, other sugars, amino acids, short chain alcohols, and volatile fatty acids. In some embodiments, modified methanogenic bacteria can utilize a subset of the aforementioned substrate forms and feedstock streams. In some embodiments, modifying the methanogenic bacteria includes making the bacteria resilient to feedstock and environmental changes. In some embodiments, the bacteria population in a feedstock milieu is highly sensitive to any changes in feedstock or the environment. Thus, in such embodiments, any changes in the feedstock or the environment could result in disruption of the anaerobic digestion processes, leading to inefficiencies. Therefore, in some embodiments of the present disclosure, the bacteria are modified in a manner such that the bacteria population is resilient enough to withstand feedstock and environmental changes without disruption (or statistically significant delay) to the anaerobic digestion processes.

In some embodiments, method 300 includes removing large solids from the feedstock mixture. In further embodiments, method 300 also includes collecting renewable energy or biochemical co-products generated from digestion of the waste material in the feedstock mixture. In such embodiments, the biochemical co-products include fertilizer, vitamins, or proteins. In some embodiments, collecting renewable energy comprises monitoring and sequestering methane and carbon dioxide generated from the blend. In some embodiments, collecting renewable energy comprises returning the sequestered carbon dioxide back into a digester as substrate for further methane production. In some embodiments, collecting renewable energy comprises subjecting gas generated to a scrubber system. In such embodiments, the scrubbed gas is stored in a fuel storage tank or converted into other forms of renewable energy. In some embodiments, collecting renewable energy comprises recovering liquefied biomass residues and residual solids for further processing into other forms of fuel or other materials for usage. In some embodiments, method 300 is performed without a pasteurization step. In other embodiments, a pasteurization step is included.

In some embodiments, method 300 includes introducing additional methanogenic bacteria into the feedstock mixture to speed up anaerobic digestion. In some embodiments, this adding of additional methanogenic bacteria can occur before or after the anaerobic digestion process has already begun.

In some embodiments, the one or more promoter substances include an enzyme that converts a portion of the biomass into promoter molecules such as cellobiose, glucose, xylose, mannose, or maltose. In some embodiments, the one or more promoter substances include the promoter molecules themselves. In some embodiments, the one or more promoter substances include a pre-treatment enzyme solution described in previous sections of the application.

In some embodiments, anaerobic digestion occurs in the presence of VFA levels above the maximum VFA level at which acidogenic bacteria can survive. As described above, acidogenesis is a common intermediate step in anaerobic digestion. Thus, in some embodiments, survival of acidogenic bacteria is useful in anaerobic digestion. However, acidogenic bacteria compete for resources with methanogenic bacteria. Thus, in some embodiments, method 300 eliminates the need for acidogenic bacteria in the anaerobic digestion processes in order to maximize methanogenic output. In some embodiments, the methanogenic bacteria attain species dominance over competing non-methanogenic bacteria in a digester so as to maximize methanogenic output.

Figure 4:
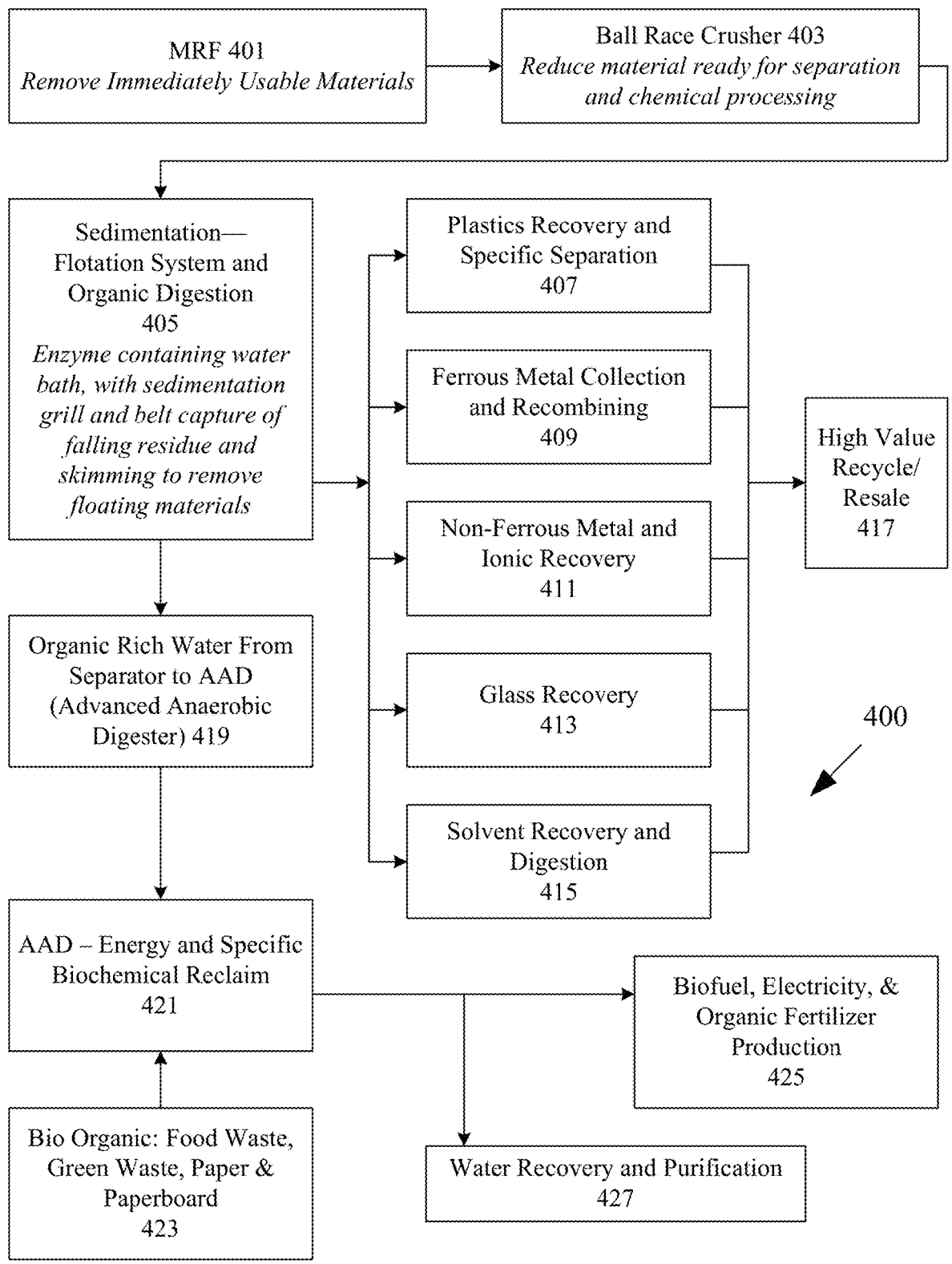
FIG. 4 is block diagram illustrating an example biochemical and engineering process for waste reclamation, in accordance with the present disclosure.

Description of FIG. 4

FIG. 4 is block diagram illustrating an example biochemical and engineering process 400 for waste reclamation, in accordance with the present disclosure. Process 400 begins with the removal of immediately usable materials 401 in a materials recovery facility ("MRF"). Next, a ball race crusher reduces the resulting material and prepares it for further separation and chemical processing 403. Subsequently, the reduced material is passed through a sedimentation and flotation system 405. In the system, a water bath containing enzymes is applied to the material, starting organic digestion, and a sedimentation grill filters certain density particles. A belt system carries the sediment residues to further processing.

After organic digestion in sedimentation and flotation system 405, sugar-rich water from the tank is passed into anaerobic digestion chamber 419. The digestate from digestate 405 is next passed to advanced anaerobic digestor ("AAD") 421. In some embodiments, bio-organic waste 423 is also introduced to AAD 421 as additional feedstock for anaerobic digestion. In some embodiments, the products produced from ADD 421 result in biofuel, electricity, and/or organic fertilizer 425. In some embodiments, water is recovered from the products of anaerobic digestion in ADD 421 and purified (427).

Solids from sedimentation and flotation system 405 are further processed into 5 different processes for processing solids. The processes correspond to further separation and recovery of 1) plastics 407, 2) ferrous metals 409, 3) non-ferrous metals 411, 4) glass 413, and 5) solvents 415, all of which can result in resalable or otherwise reusable materials 417.

Figure 5:
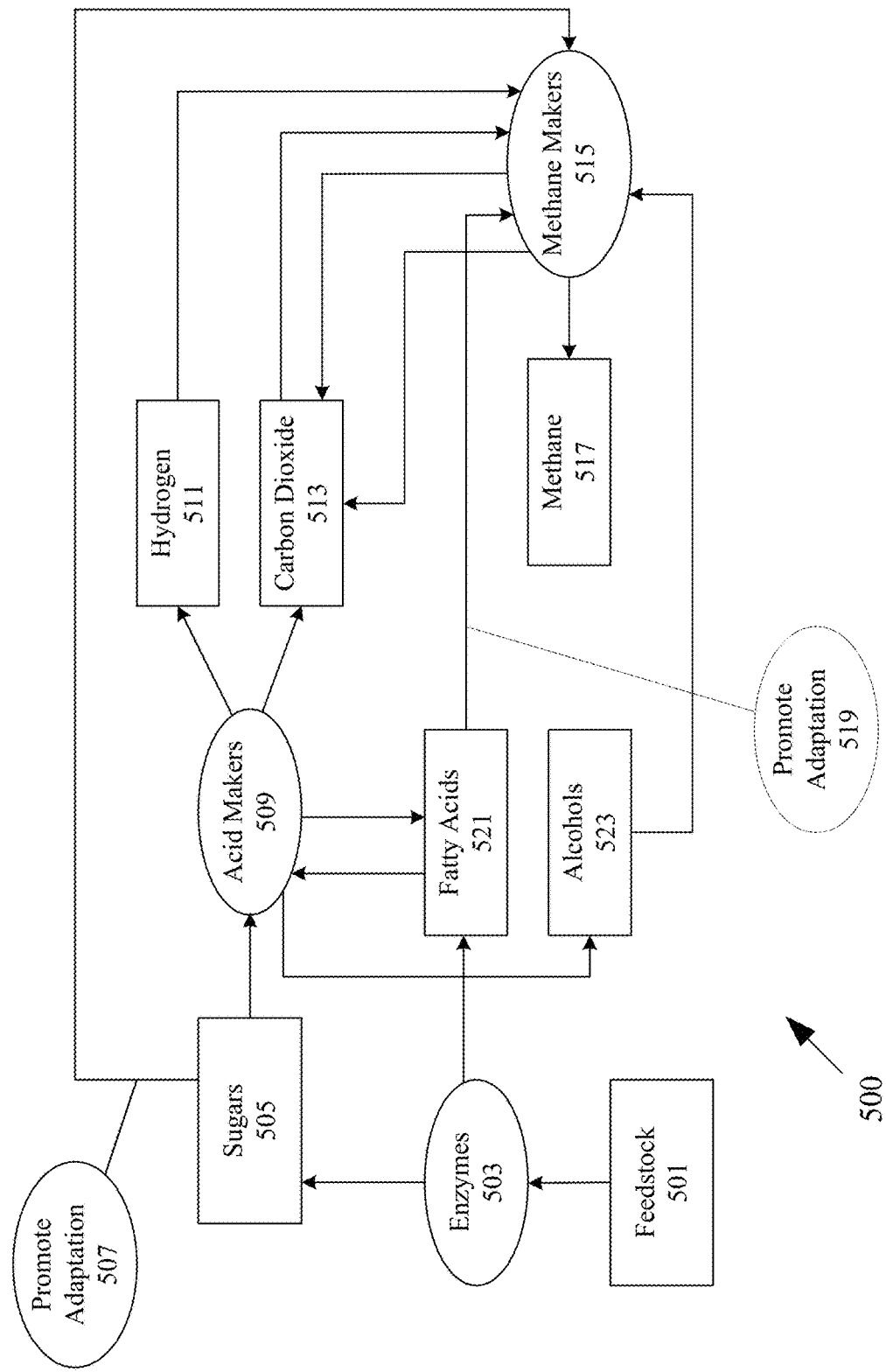
FIG. 5 is a block diagram illustrating an example process of anaerobic digestion, in accordance with the present disclosure.

Description of FIG. 5

FIG. 5 is a block diagram illustrating an example process 500 of anaerobic digestion, in accordance with the present disclosure. Process 500 begins with feedstock 501. As mentioned above, feedstock 501 can include any bioorganic materials present in waste including but not limited to municipal solid waste, manure or sewage, garden clippings, or agricultural crops. With the introduction of enzymes 503, sugars 505 and fatty acids 521 are released. In some embodiments, the enzymes can be any of the enzymes described above, including the enzymes used in pre-treatment solutions described previously in the application. In some embodiments, the treatment of enzymes 503 promotes the adaptation 507 of methanogens 515. In some embodiments, the sugars are also utilized by acid makers 509 and are metabolized into four categories: hydrogen 511, carbon dioxide 513, fatty acids 521, and alcohols 523. All of these four categories are utilized by the methane makers 515. In some embodiments, acid makers 509 metabolize sugars into a subset of the four categories listed. In some embodiments, acid makers 509 metabolize sugars into other products not listed. Fatty acids 521 also induce adaptation 519 by the methanogens 515. Finally, the methanogens release methane 517 and carbon dioxide 513.

Example of a Waste Conversion System

Next, an example of a waste conversion system, with machine parts and incorporating biochemical processes, is described in detail. Many of the steps correspond to the method steps described above. The following example system is one possible embodiment of a system as provided in the present disclosure and is not meant to be binding. Each machine part can be a standard machine part known to those of ordinary skill in the art and thus, figures of such machine parts are unnecessary for understanding of the methods and systems described in the present disclosure.

First, municipal solid waste is shredded or otherwise reduced into smaller-sized fragments and introduced to a receiving receptacle. In some embodiments, the fragments are no greater than 0.25 sq. in. The waste then flows to two mixing vessels, where it is mixed with water. In some embodiments, the temperature of the water is at either 50 or 37 degrees Celsius, delivered from a fresh water tank via a boiler. In some embodiments, a specific enzyme mixture from an enzyme enclosure is also mixed in. In the mixing tanks, initial release of soluble sugars commences, derived as beta 1-4 linked units or monosaccharide moieties. In some embodiments, pre-treatment solutions can cause soluble sugars to be released earlier and/or in higher quantities. The mixtures then flow from the mix tanks to their respective anaerobic digester tanks, where methanogenic microbes are added either endemically or from fermenters via a microbe enclosure. In some embodiments, the methanogenic bacteria are pre-treated by a solution of enzymes prior to being added to the digester tanks. These microbes utilize the sugars themselves, or carboxylic acids and esters as carbon sources, ultimately reducing them to methane and oxidizing them to carbon dioxide. In some embodiments, gases generated within the anaerobic digester tanks are passed through scrubbers to remove hydrogen sulfide and carbon dioxide. In such embodiments, the residual methane-rich gas is then passed to a dryer and then to a compressor to be pumped at constant pressure to a microturbine or Piston or rotary generator. Alternatively, the gas can be stored or compressed to form a liquid fuel. In some embodiments, excess gas is flared. In some embodiments, the residual gas is passed through a heat exchanger to recover the heat which is then used to heat the boiler to provide warm water for the system. In some embodiments, the electricity generated by the microturbine is passed to a switchgear for various applications.

In some embodiments, the digestate mixture from the anaerobic digestors is separated into liquid and solid materials. The solid materials in one embodiment may be consolidated and applied as fertilizer in liquid suspension. In a further embodiment, the solids may be compressed and used for construction. In yet a further embodiment, the solids may be compressed as briquettes or powdered to be used as fuel in biomass boiler systems. The water is passed to filtration and then pumped to a recycled water tank for holding. This water is then passed for purification via reverse osmoses and then returned to the fresh water tank for reuse. Solids which are not digested in the mix tanks are recovered to a solids removal bin and from there taken for separation into recoverable commodities.

Advantages

There are several advantages to enzymatic treatment in anaerobic digestion. Thus, generation of gas per unit input is increased. Many of the advantages described herein are possible examples of advantages conferred by the methods and systems described in the present disclosure and are not necessarily applicable to every embodiment in accordance with the present disclosure. For example, one advantage is an increase in biogas volume per unit feedstock is realized between 30% and 250% above conventional anaerobic digestion not treated with enzymes.

Another advantage is the reduction in necessary hydraulic retention time, or the recovery time after disruption (due to the introduction of a noxious substance or change in the environment or feedstock), of the system. For example, using methods of the present disclosure, the hydraulic retention time can be reduced from 60 days to 5 days. Also, the system is more resilient to environmental changes, such as temperature and pH change. Conventionally, thermophilic bacteria present after pasteurization cannot withstand any wavering of temperature on the order of 1 or 2 degrees in either direction, or a pH variance of 1.2. However, in some embodiments, the methanogenic bacteria in the systems and methods of the present disclosure can tolerate a temperature range of 0 to 50 degrees C. and a pH range from 5.5 to 8.5.

Yet another advantage is the reduction of the size of equipment. For example, a digester in accordance with embodiments of the present disclosure can produce the same gas output as a conventional digester that is two and a half times its size.

In addition, another advantage of enzymatic treatment is the increased variation in usable feedstock. Conventionally, feedstock is starch based and/or waste food material and/or manure. Any change of feedstock causes significant change in output and possibly collapse. However, in some embodiments, feedstock can be any waste material and thus, a change will have no significant effect on the anaerobic digestion system.

Yet another advantage of the methods of the present disclosure is the use of the full range of methanogenic bacteria normally resident in the waste material, while improving efficiency. For example, in some embodiments, at least 9 different strains of bacteria were found to be utilized by the system. Additionally, they promote an overall broadening of the capacity of the organisms to metabolise a wider range of feedstock types. This enhances their output of methane by enabling them to access more of the carbon available in a variety of forms—ranging from sugars, to fatty acids, to amino acids, to carbon dioxide. In some embodiments, this change occurs across all or most methanogenic populations present and is not limited to a single species. Consequently, the increase in methane generation is not limited to a single species and the maintenance of the methanogenic species diversity within the digester, combined with the wider range of ability to deal with different substances as carbon sources, results in a much increased resilience to substrate change or toxic insult to the digester. In some embodiments, the greater access to energy rich carbon compounds in turn stimulates the rate of methanogen replication and thereby a steep population rise, again leading to an exponential increase in methane output, coincident with the exponential population rise in addition to the rise referred to earlier, due to the greater access of the original methanogenic populations to the available carbon sources.

Another advantage of the methods of the present disclosure is the reduction in then activity of bacteria competing with the methanogenic archaea and bacteria within the digester milieu by causing the competing bacteria to rapidly produce carboxylic acids such that rise in concentration to levels that cause reduced activity of the organisms producing them. One possible overall effect is the generation of a diverse methanogenic community, adapted to a wide range of substrate forms and resilient to feedstock and environmental change, with a consequent high growth rate and suffering little competition. In some embodiments, this leads to a much enhanced output per unit input with wide feedstock acceptance and high resilience to change. As mentioned above, this promoter modification of the methanogenic bacteria allows for the avoidance of the need for pasteurization to reduce their activity in competition with the methanogenic archaea and bacteria. In some embodiments, the lack of a pasteurization step also leads to bacterial diversity, since pasteurization would necessarily select just a few strains out of the many possible strains resident in the waste. This is because the high heat also kills off the majority of the methanogenic bacteria along with the competing bacteria, leaving only 1 or 2 thermophilic strains, which is wasteful and highly unstable.

Yet another advantage of the methods in the present disclosure is the actual generation of fuel and fertilizer through the digestion of waste. Yet another advantage is the long term microbial adaptation and microbial community changes that are engendered in the improved anaerobic digestion processes described above to amplify and accelerate fuel output.

In various embodiments, the methods follow standard ecological processes, meaning the bacteria are not genetically modified. Thus, the system is more stable because genetically modified organisms are typically just one strain, whereas as aforementioned, the methods of the present disclosure result in the utilization of a wide range of methanogenic bacterial strains. However, in other embodiments, the bacteria itself is genetically modified, in accordance with the methods and systems provided in the present disclosure.

Although the figures in the present disclosure show specific exemplary embodiments of the present disclosure, the figures are intended more as functional descriptions of the various features, which may be present in systems in accordance with the present disclosure, than as structural schematics of the embodiments described herein. In practice, and as recognized by those of ordinary skill in the art, items shown separately could be combined and some items could be separated. For example, some items shown separately in the figures could be implemented without certain elements or with more elements that have not been shown. In addition, the actual number of elements used to implement a waste management and renewable energy system and how features are allocated among them will vary from one implementation to another.

The foregoing description, for purpose of explanation, has been described with reference to specific embodiments. However, the illustrative discussions above are not intended to be exhaustive or to limit the present disclosure to the precise forms disclosed. Many modifications and variations are possible in view of the above teachings. The embodiments were chosen and described in order to best explain the principles of the present disclosure and its practical applications, to thereby enable others skilled in the art to best utilize the present disclosure and various embodiments with various modifications as are suited to the particular use contemplated.

What is claimed is:

1. A method for improved anaerobic digestion, the method comprising:

introducing one or more promoter substances to a feedstock mixture, the feedstock mixture including prokaryotic microorganisms, the one or more promoter substances being capable of modifying the prokaryotic microorganisms without genetically modifying the prokaryotic microorganisms, wherein modifying the prokaryotic microorganisms includes stimulating novel enzyme production for methanogenesis such that the prokaryotic microorganisms attain species dominance over competing non-methanogenic bacteria.

2. The method of claim 1, wherein the feedstock mixture is made from mixture of waste material and water.

3. The method of claim 2, including collecting renewable energy or biochemical co-products generated from digestion of the feedstock mixture.

4. The method of claim 3, wherein the biochemical co-products include fertilizer, vitamins, or proteins.

5. The method of claim 3, wherein collecting renewable energy comprises:

monitoring and sequestering methane and carbon dioxide generated from the feedstock mixture; and returning the sequestered carbon dioxide back into a digester as substrate for further methane production.

6. The method of claim 3, wherein collecting renewable energy comprises:

subjecting gas generated to a scrubber system; and storing scrubbed gas in a fuel storage tank or converting the scrubbed gas into other forms of renewable energy.

7. The method of claim 3, wherein collecting renewable energy comprises recovering liquefied biomass residues and residual solids for further processing into other forms of fuel or other materials for usage.

8. The method of claim 1, wherein the prokaryotic microorganisms are pre-treated with a solution of enzymes before any anaerobic digestion processes occur.

9. The method of claim 1, wherein modifying the prokaryotic microorganisms includes increasing an expression rate of already expressed genes to a level higher than that of prokaryotic microorganisms not exposed to the one or more promoter substances or stimulating an expression of genes useful for anaerobic digestion that are unexpressed in prokaryotic microorganisms not exposed to the one or more promoter substances.

10. The method of claim 1, wherein the prokaryotic microorganisms are cultured from resident populations in the feedstock mixture so as to reduce barriers to bacterial adaptation to the feedstock mixture.

11. The method of claim 1, including introducing additional prokaryotic microorganisms into the feedstock mixture to speed up anaerobic digestion.

12. The method of claim 1, wherein modifying the prokaryotic microorganisms includes modifying the prokaryotic microorganisms in a way as to eliminate a need for acidogenesis to occur more than once or the need to even occur at all during the methanogenesis.

13. The method of claim 1, wherein the one or more promoter substances includes an enzyme that converts a portion of biomass into promoter molecules including cellobiose, glucose, xylose, mannose, or maltose or wherein the one or more promoter substances includes promoter molecules themselves.

14. The method of claim 1, wherein anaerobic digestion occurs when VFA levels are above a maximum VFA level at which acidogenic bacteria can survive.

15. The method of claim 1, wherein the prokaryotic microorganisms attain species dominance over other microorganisms in a digester.

16. The method of claim 1, wherein the one or more promoter substances leads to fatty acid production in concentration levels above maximum levels that are tolerable for acidogenic bacteria.

17. The method of claim 1, wherein the method is performed without a pasteurization step.

18. The method of claim 1, wherein at least some of the modified prokaryotic microorganisms are adapted to utilize directly as a food source a wide range of substrate forms and feedstock streams, including oligosaccharides, polysaccharides, monosaccharides, other sugars, amino acids, short chain alcohols, and volatile fatty acids.

19. The method of claim 1, wherein the feedstock mixture includes a mixed waste stream containing both bio-organic and non-bio-organic material, wherein the non-bio-organic material is separated from the feedstock mixture and processed into forms suitable for reuse.

20. A system for improved anaerobic digestion, the system comprising machinery configured to:

introduce one or more promoter substances to a feedstock mixture, the feedstock mixture including prokaryotic microorganisms, the one or more promoter substances being capable of modifying the prokaryotic microorganisms without genetically modifying the prokaryotic microorganisms, wherein modifying the prokaryotic microorganisms includes stimulating novel enzyme production for methanogenesis such that the prokaryotic microorganisms attain species dominance over competing non-methanogenic bacteria.

* * * * *